(12) United States Patent
Krausman et al.

(10) Patent No.: US 6,306,088 B1
(45) Date of Patent: Oct. 23, 2001

(54) AMBULATORY DISTRIBUTED RECORDERS SYSTEM FOR DIAGNOSING MEDICAL DISORDERS

(75) Inventors: David T. Krausman, Kingsville; Richard P. Allen, Arnold, both of MD (US)

(73) Assignee: Individual Monitoring Systems, Inc., Baltimore, MD (US)

( * ) Notice: Subject to any disclaimer, the term of this patent is extended or adjusted under 35 U.S.C. 154(b) by 0 days.

(21) Appl. No.: 09/185,055

(22) Filed: Oct. 3, 1998

(51) Int. Cl.[7] ........................................................ A61B 5/00
(52) U.S. Cl. .......................... 600/301; 600/523; 600/534; 600/483
(58) Field of Search ...................................... 600/522, 532, 600/483, 301, 300, 306, 323, 324, 547, 544, 546, 534; 607/902

(56) References Cited

U.S. PATENT DOCUMENTS

| | | | |
|---|---|---|---|
| 4,129,125 | 12/1978 | Lester et al. | 128/2.05 |
| 4,784,162 | 11/1988 | Ricks et al. | 128/903 |
| 4,886,064 | * 12/1989 | Strandberg | 128/903 |
| 4,909,260 | 3/1990 | Salem et al. | 128/721 |
| 4,966,155 | 10/1990 | Jackson | 128/671 |
| 4,999,772 | 3/1991 | Bowman et al. | 364/413.05 |
| 5,275,159 | 1/1994 | Griebel | 128/633 |
| 5,611,349 | 3/1997 | Halleck et al. | 128/721 |
| 5,682,898 | 11/1997 | Aung et al. | 128/671 |
| 5,732,709 | 3/1998 | Tacklind et al. | 128/726 |
| 5,738,102 | 4/1998 | Lemelson | 128/671 |
| 5,765,563 | 6/1998 | Vander Schaaf | 128/725 |
| 5,899,855 | * 5/1999 | Brown | 600/301 |
| 5,902,250 | * 5/1999 | Verrier et al. | 600/515 |
| 5,957,854 | * 9/1999 | Besson et al. | 600/509 |

* cited by examiner

*Primary Examiner*—Kennedy Schaetzle
(74) *Attorney, Agent, or Firm*—Larry J. Guffey

(57) ABSTRACT

The present invention provides a method and apparatus for diagnosing of the medical condition of a fully ambulatory subject who exhibits temporal variations in various physiological parameters as a result of the subject's medical condition. The method comprises the steps of (1) locating a separate, self-contained, recording unit on a plurality of selected measurement sites of the subject, (2) using these units to collect sensor output data, (3) sampling this sensor output data at prescribed time intervals, (4) time stamping and storing this sampled data in recording, (5) transferring this data via a smart input/output interface device to an external computer, and (6) using the external computer with appropriate application software to analyze and diagnose the medical condition of the subject. A system of recording units is disclosed for an embodiment of the present invention directed at diagnosing subjects exhibiting sleep disorders.

11 Claims, 14 Drawing Sheets

AMBULATORY DISTRIBUTED RECORDERS SYSTEM FOR DIAGNOSING MEDICAL DISORDERS

BACKGROUND OF THE INVENTION

1. Field of the Invention

The present invention generally relates to physiological monitoring devices. More particularly, this invention relates to two or more site-specific recorders and the method for monitoring, recording and analyzing the medical disorders of a fully ambulatory subject.

2. Description of the Related Art

The diagnosis of sleep disorders often involves polysomnopgraphy (PSG), the monitoring and recording over an extended period of time of the temporal variations in the amplitude of the patient's sleep-impacted, physiological parameters, including: heart rate, eye blink activity, airflow rate, thorax and abdomen respiration rates, the blood's oxygen saturation level, electroencephalograms (EEG), electrooculorgrams (EOG), and electromyograms (EMG). Such intensive monitoring activities are typically conducted in clinical settings by trained PSG technicians who utilize expensive monitoring equipment having multiple sensors that are tethered to a centralized recording system and power supply.

For several decades, the recordings of such physiological parameters were provided by strip chart recorders that produced long strips of paper with ink markings that displayed the varying physiological parameters. The clinician would then examine such records and "score" each abnormal sleep event that occurred. This practice continues today with the clinician now viewing computer screens displaying the varying physiological parameters.

More recently, a number of portable recording systems for screening and diagnosing sleep disorders have been marketed. These systems range from multi-channel, PSG-style systems to much simpler units that monitor only one or more of the possible physiological parameters of interest. However, these multi-channel, portable systems remain technically complex, expensive and usually require trained PSG technicians to supervise their use. The complexity of the tethered sensors and electrode wires that are used with these multi-channel, portable systems is shown in FIG. 1.

Some of the newer of these portable systems offer comprehensive software for display and analysis of the collected sleep data, and some offer automatic sleep event scoring. However, such scoring has been found to have varying degrees of reliability due to the technical problems associated with assuring good signal fidelity in the monitored parameters. Thus, all of these systems recommend for accurate identification of abnormal sleep events that the data be interpreted and evaluated by experienced clinicians or trained PSG technicians.

The nature of PSG signal fidelity problems is seen in FIG. 2 which shows the tracings provided by the manufacturer of the portable system shown in FIG. 1 for the temporal variations in airflow and respiration sensors located respectively at the patient's (1) mouth and nasal passageway, (2) chest, and (3) abdomen. Both the chest and abdomen sensors show poor signal fidelity and the abdomen signal is amplitude clipped and distorted. The two respiration signals are time shifted about five percent, while the airflow signal is shifted about fifteen percent.

Since PSG scoring is largely subjective, experienced scorers can generally interpret with good accuracy the action and interactions of poorly shaped and time skewed signals. Although these distortions are commonly accepted as normal for manual scoring, such poor fidelity signals would be unsatisfactory for automated or computer-based scoring.

All of the current, portable sleep testing systems share common, less-than-desirable features for home use: (1) they are bedside portable, but their size and weight does not allow the patient to be ambulatory, which can be essential for diagnosing patients problems such as excessive sleepiness, (2) they are not designed for unattended use—a technician must come to the home for set-up, disconnection and data retrieval, (3) patients must be outfitted with an array of tethered electrode wires and sensors for connection to bulky body monitors or table-top consoles, and (4) most require subjective analysis of the data by highly trained, sleep professionals.

Recognizing the need for an improved apparatus or method for diagnosing of the various medical conditions of a fully ambulatory subject who exhibits temporal variations in various physiological parameters as a result of this medical condition, it is therefore a general object of the present invention to provide a novel method and ambulatory, distributed recorders system to meet such needs.

SUMMARY OF THE INVENTION

The present invention is generally directed to satisfying the needs set forth above and the problems identified with physiological parameter monitoring systems. The problems, of having to harness the to-be-monitored subject to laboratory recording equipment and the monitor's insufficient response capabilities to the data being collected, are resolved by the present invention.

In accordance with one preferred embodiment of the present invention, the foregoing need can be satisfied by providing a method for aiding in the diagnosis of the medical condition of a fully ambulatory subject who exhibits temporal variations in various physiological parameters as a result of said medical condition, the method comprising the steps of (1) locating a separate, self-contained, recording unit on a plurality of selected measurement sites of the subject, wherein these recording units are each battery operated and have a physiological parameter sensor with appropriate signal conditioning and filtering circuitry to yield required levels of signal fidelity., a programmable controller with an analog to digital converter and an integrated data storage recorder, (2) using these units to collect sensor output data that quantifies the temporal variations in the physiological parameter of interest at each measurement site, (3) sampling this sensor output data at prescribed time intervals, (4) time stamping and storing this sampled data in the integrated recorders, (5) transferring this data via a smart input/output interface device that controls the flow of data between the recorders and an external computer, while allowing for the time synchronization of the collection of data with these units, and (6) using the external computer with application software to analyze and display the temporal variations in the data for the purpose of diagnosing the medical condition of the subject.

In another preferred embodiment, the present invention is seen to take the form of an ambulatory, distributed recorders system. It comprises several, separate, miniature, self-contained, recording units which may be located at various body sites where specific physiological parameters are to be monitored. Each such unit contains a recorder and power supply, wherein one or more sensors for the desired physiological parameter to be monitored are integrated into the recorder.

Various embodiments of the present invention are created when such systems are directed at diagnosing various medical conditions which call for the monitoring of differing physiological parameters, and thus the use of various types of sensors and recorder units. Additionally, it should be noted that the nature of the present invention is open ended, in that other distributed recording units, such as: (1) an ambulatory pulse oximeter unit worn on the wrist with a corresponding finger probe for measuring and recording both oxygen saturation of the blood (SaO2) and pulse rate, (2) a head gear apparatus with attached, non-tether EEG electrodes and an integral recording device for measuring electroencephalogram signals of the brain, (3) an EMG recorder configuration with attached, non-tethered electrodes for electromyographic recording of muscle activity at various locations of the body, (4) a self-contained, accelerometer-based movement recording device worn on the limbs or other body sites to measure tremor frequency and the power components of body movements for disorders such as Parkinson's Tremor, Essential Tremor, Tartive Dyskinesia and various other movement maladies or (5) a cardiac recording unit which records a cardiac signal, may be added to the system when the technical problems associated with the miniaturization of the necessary sensor; and their integrated recorders are overcome.

In an embodiment of the present invention that is directed at monitoring, recording and analyzing the sleep disorders of a fully ambulatory subject, the measurement sites where appropriately designed recorder units are placed and the related physiological parameters of interest at these sites are chosen from the group consisting of (1) chest—respiration effort, activity level and body position., (2) abdomen—respiration effort, (3) head—airflow and eye blink phenomena, (4) wrist—activity level, and (5) ankle—periodic leg movement.

Other objects and advantages of this invention will become readily apparent as the invention is better understood by reference to the accompanying drawings and the detailed description that follows.

DESCRIPTION OF THE PREFERRED EMBODIMENT

Figure 3:
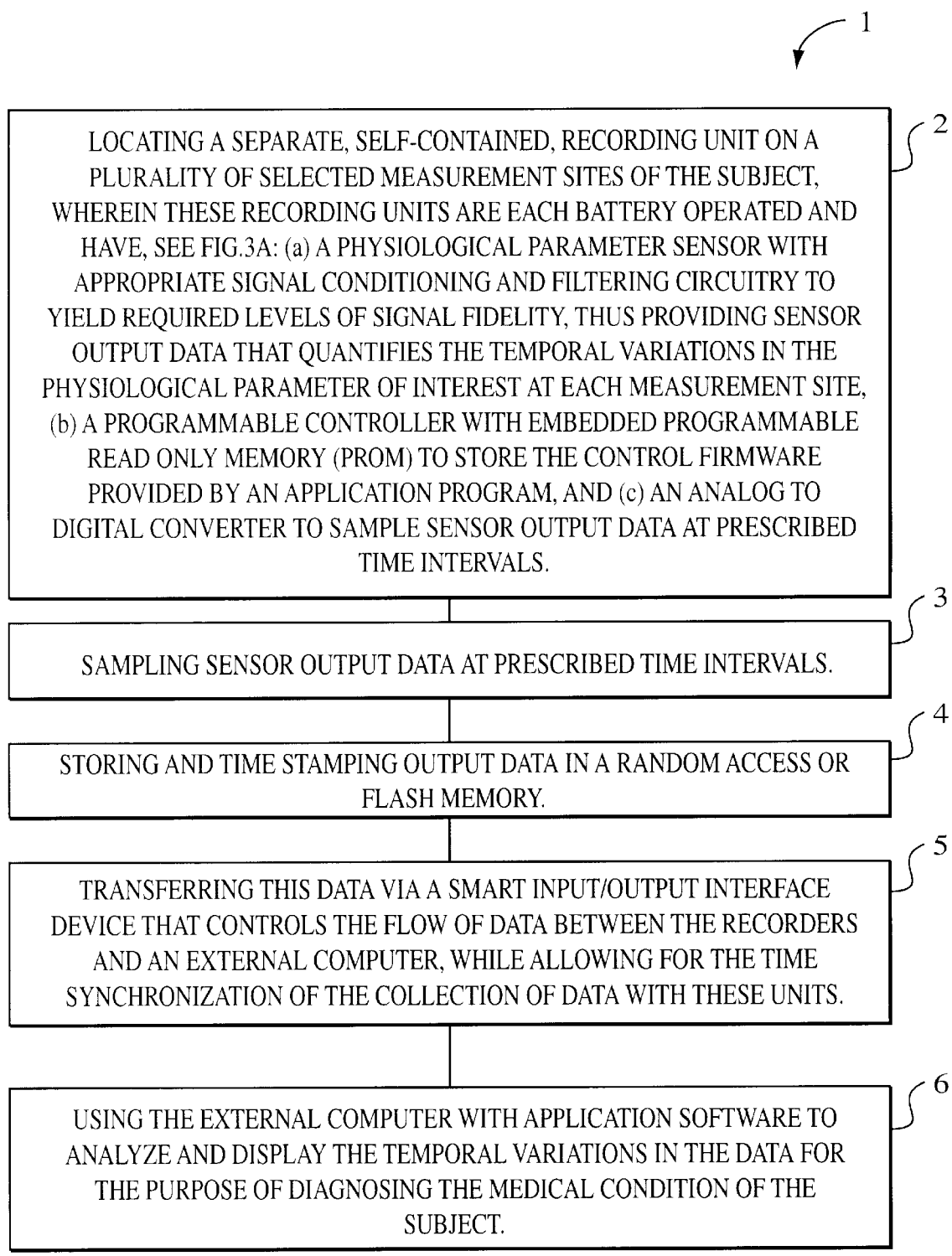
FIG. 3 is a schematic flow diagram which depicts a method in accordance with a preferred embodiment of the present invention.

Referring now to the drawings wherein are shown preferred embodiments and wherein like reference numerals designate like elements throughout, there is shown in FIG. 3 a schematic flow diagram which depicts a method in accordance with a preferred embodiment of the present invention for aiding in the diagnosis of the medical condition of a filly ambulatory subject who exhibits temporal variations in various physiological parameters as a result of said medical condition.

Figure 3A:
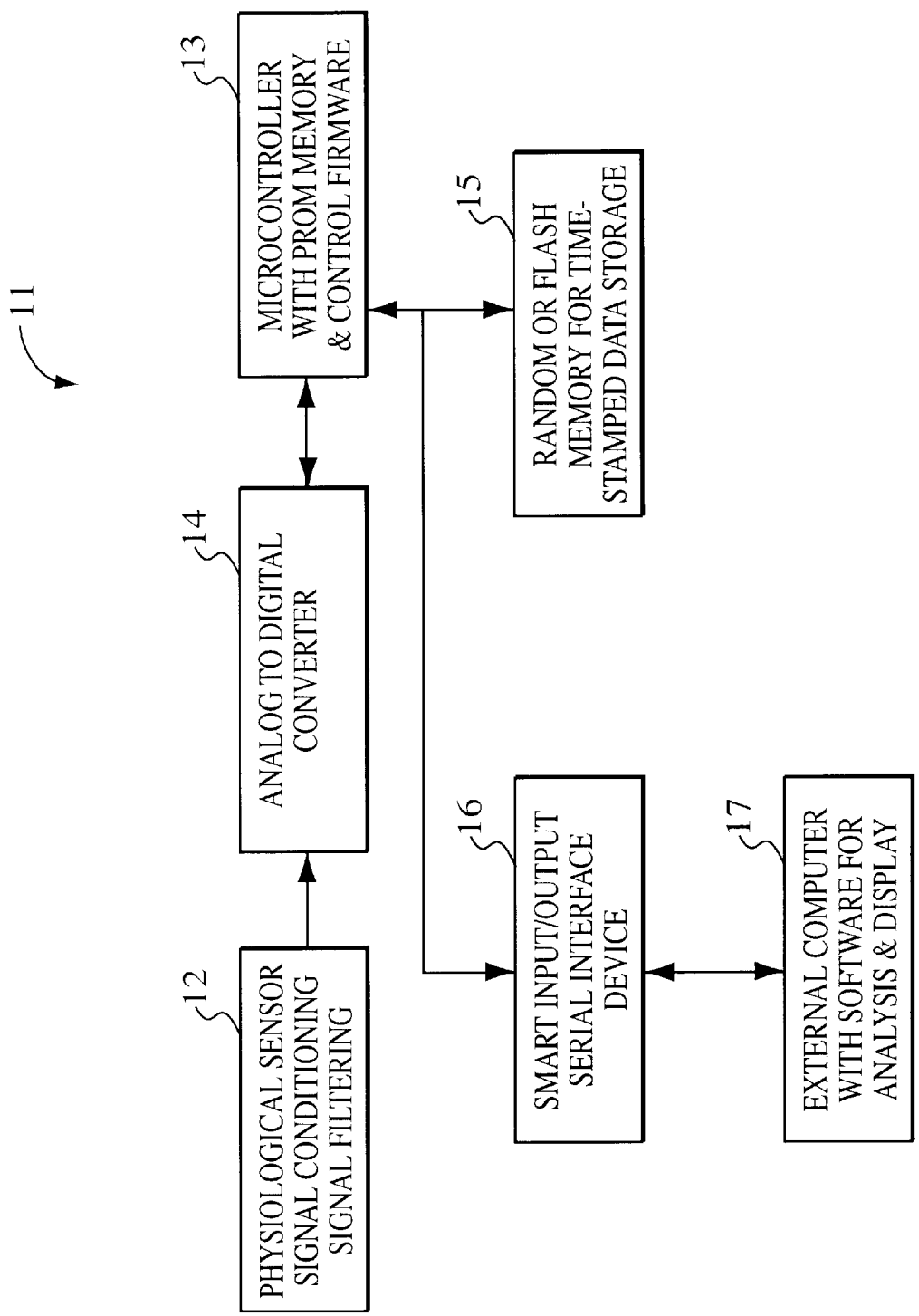
FIG. 3A is a schematic flow diagram of the basic recorder unit of the present invention.

In this embodiment, the method 1 is seen to comprise the steps of (1) locating 2 a separate, self-contained, recording unit 11 on a plurality of selected measurement sites of the subject, wherein these recording units, see FIG. 3A, are each battery operated and have: (a) a physiological parameter sensor 12 with appropriate signal conditioning and filtering circuitry to yield required levels of signal fidelity, thus providing sensor output data that quantifies the temporal variations in the physiological parameter of interest at each measurement site, (b) a programmable controller 13 with embedded programmable read only memory (PROM) to store the control firmware provided by an application program, and (c) an analog to digital converter 14 to sample sensor output data at prescribed time intervals, (2) sampling 3 sensor output data at prescribed time intervals, (3) storing and time stamping 4 output data in a random access or FLASH memory 15, (4) transferring 5 this data via a smart input/output interface device 16 that controls the flow of data between the recorders and an external computer 17, while allowing for the time synchronization of the collection of data with these units, and (5) using 6 the external computer with application software to analyze and display the temporal variations in the data for the purpose of diagnosing the medical condition of the subject.

Figure 4:
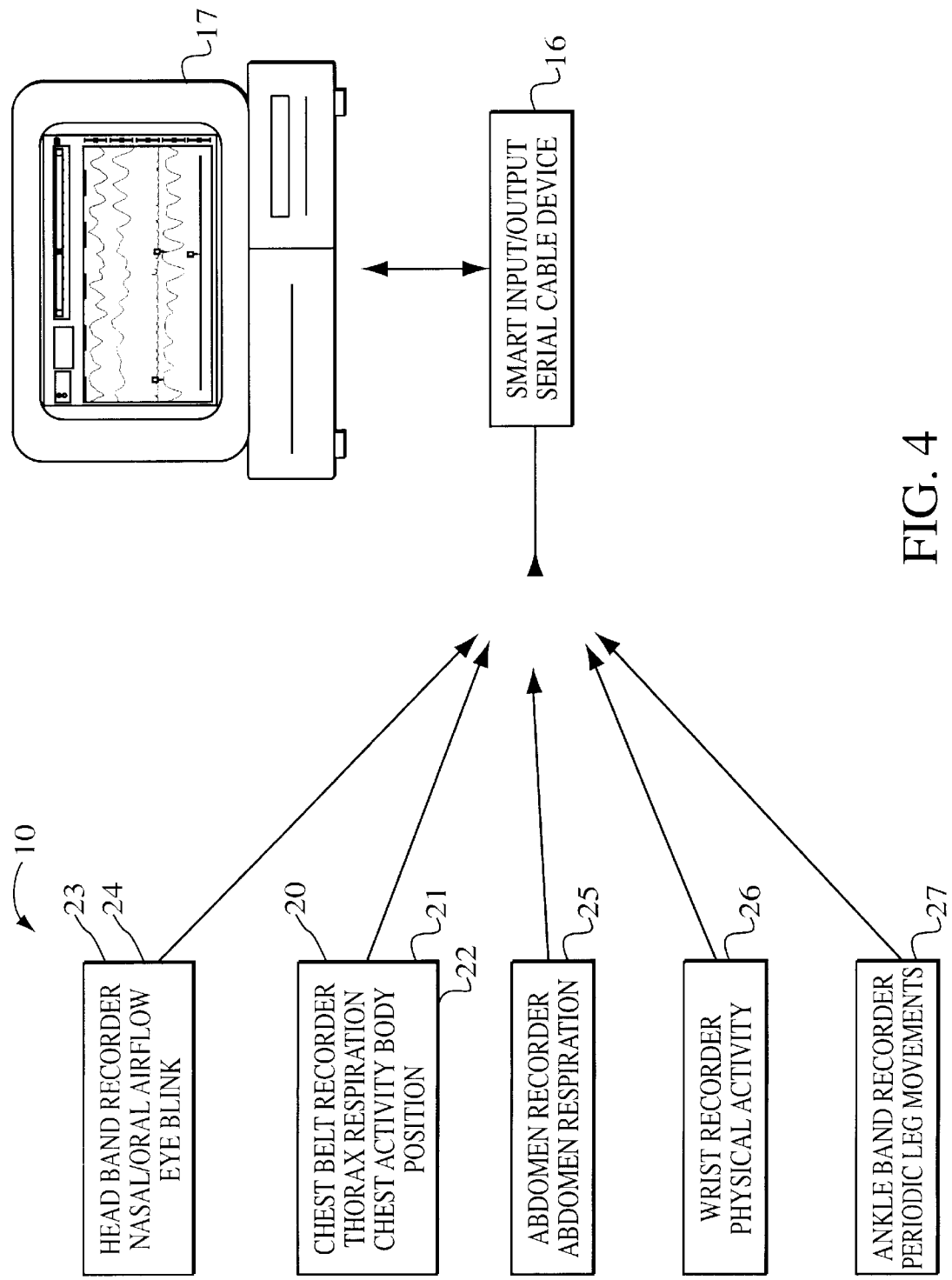
FIG. 4 is a schematic block diagram of an ambulatory, distributed recorders system in accordance with a preferred embodiment of the present invention.

In another preferred embodiment, the present invention is seen to take the form of an ambulatory, distributed recorders system 10. A general overview of this embodiment is shown in FIG. 4 which provides a schematic block diagram of the system. It comprises several, separate, miniature, self-contained, recording units 11 which may be located at various body sites where specific physiological parameters are to be monitored. Each such unit contains a recorder and power supply, wherein one or more sensors for the desired physiological parameter to be monitored are integrated into the recorder.

Various embodiments of the present invention are created when such systems are directed at diagnosing various medical conditions which call for the monitoring of differing physiological parameters, and thus the use of various types of sensors and recorder units.

For an embodiment of the present invention directed to the diagnosis of fully ambulatory patients with a sleep disorder or excessive sleepiness, PSG data is collected by a system which uses the following recording units at the body locations indicated:

| Body Location | Recorder | Clinical Utility |
| --- | --- | --- |
| Chest belt | Respiration Effort 20 | Sleep Apnea |
| | 3D Body Position 21 | Sleep Apnea & Sleep State |
| | Chest Activity 22 | Sleep-Wake State & Continuity |
| Head Band | Air Flow 23 | Sleep Apnea |
| | Optional - Eye Blink 24 | Sleep-Wake State & Continuity, REM Identification |
| Abdominal Belt | Respiration Effort 25 | Sleep Apnea |
| Wrist Band | Physical Activity 26 | Sleep-Wake State & Continuity |
| Ankle Band | Periodic Movement 27 | Periodic Leg Movement |

Additionally, it should be noted that the nature of the present invention is open ended, in that other distributed recording units, such as: (1) an ambulatory pulse-oximeter unit worn on the wrist with a corresponding finger probe for measuring and recording both oxygen saturation of the blood (SaO2) and pulse rate, (2) an electroencephalogram unit comprising a head gear apparatus with attached, non-tether EEG electrodes and an integral recording device for measuring electroencephalogram signals of the brain, (3) an EMG recorder unit with attached, non-tethered electrodes for electromyographic recording of muscle activity at various locations of the body, (4) body motion frequency unit comprising a self-contained, accelerometer-based movement recording device worn on the limbs or other body sites to measure tremor frequency and the power components of body movements for disorders such as Parkinson's Tremor, Essential Tremor, Tartive Dyskinesia and various other movement maladies, or (5) a cardiac recording unit which records a cardiac signal, may be added to the system for monitoring sleep or other medical disorders when the technical problems associated with the miniaturization of the necessary sensors and their integrated recorders are overcome.

Figure 5:
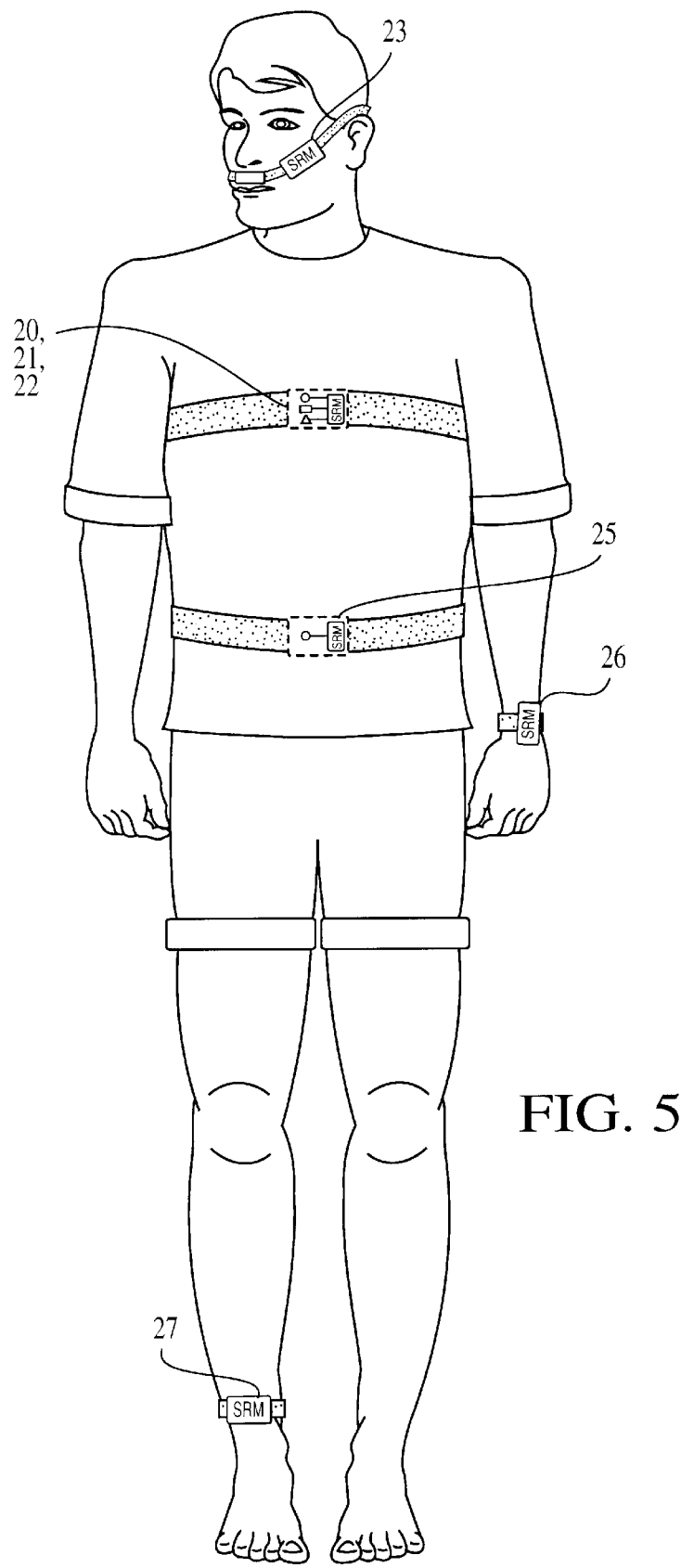
FIG. 5 shows the placement of the recorders for a system designed for monitoring ambulatory patients exhibiting excessive sleepiness.

FIG. 5 illustrates the placement of these units on a patient. The recorder on the chest belt is seen to record the signals from three individual sensors.

This system, except for the optional Eye Blink and Air Flow recorder which have short wires running from the head band to small sensors, has little if any wiring running around the body connecting sensors to recorders and it has no components such as electrodes which require technician assistance for placement or for maintenance during recording. Since each of the recorder units provides a miniaturized combination of sensor and recorder, there is little problem with patient discomfort, nothing for the patient to do aside from put on the monitors and no problem with the patient wearing the units at all times during sleep.

The units each provide digital storage of data from a recording of a full night's sleep or the recording over other extended periods (e.g., 24 hour monitoring) and provide for transfer of the data to a host computer for analysis. An application program contained in the host computer is used to initialize all the recorders. This operation clears the unit's memory and transports header information from the external host computer to the various recorders. This information includes: current time, date, unit number, start time and stop time. The smart serial cable interface initializes each recorder individually and sets a delayed start time for the exact starting of each of the recorders for lock-step synchronization. The various recorded signals are displayable on the host computer in a multi-channel, analog format for analysis.

Figure 12:
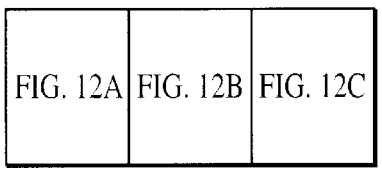
FIG. 12 is the schematic circuit diagram for the head band worn recording unit. The circuit shown is a basic representation of the other system recorders which are configured to accept appropriate sensors for various physiological measures and provide similar functional components.
Figure 12A:
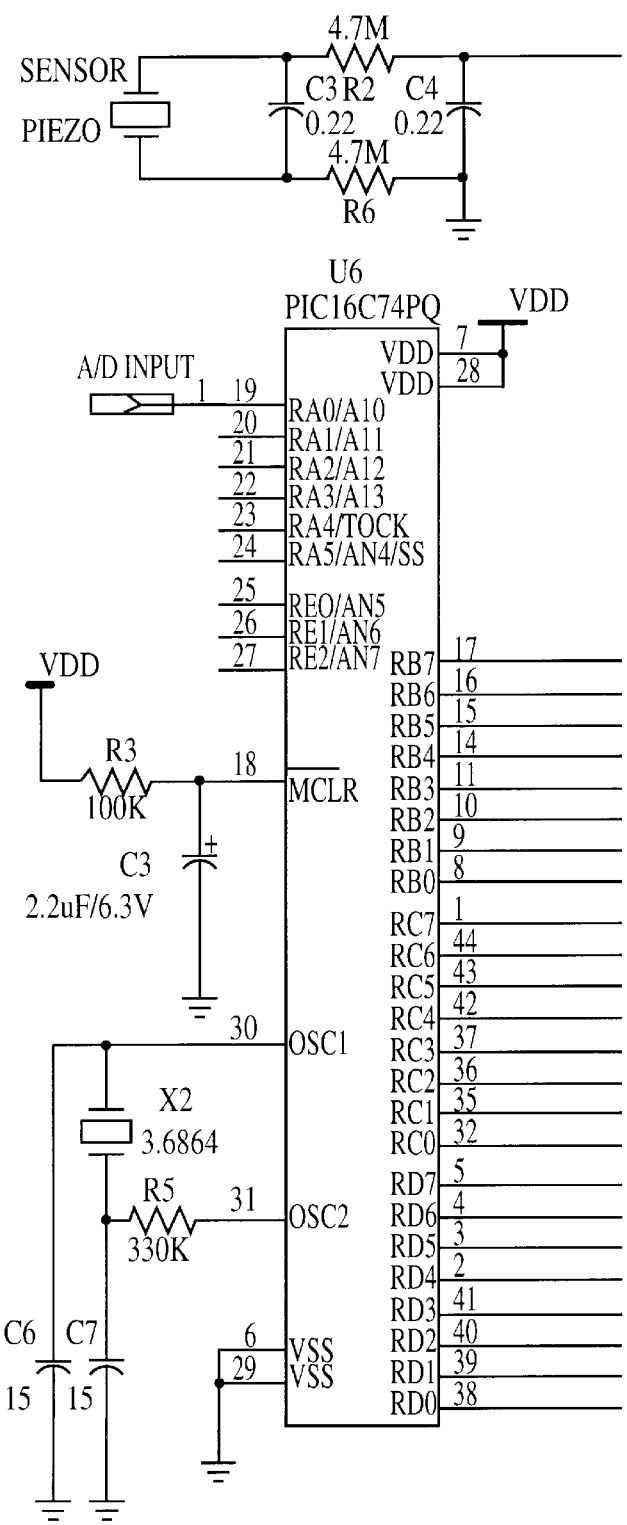
Figure 12B:
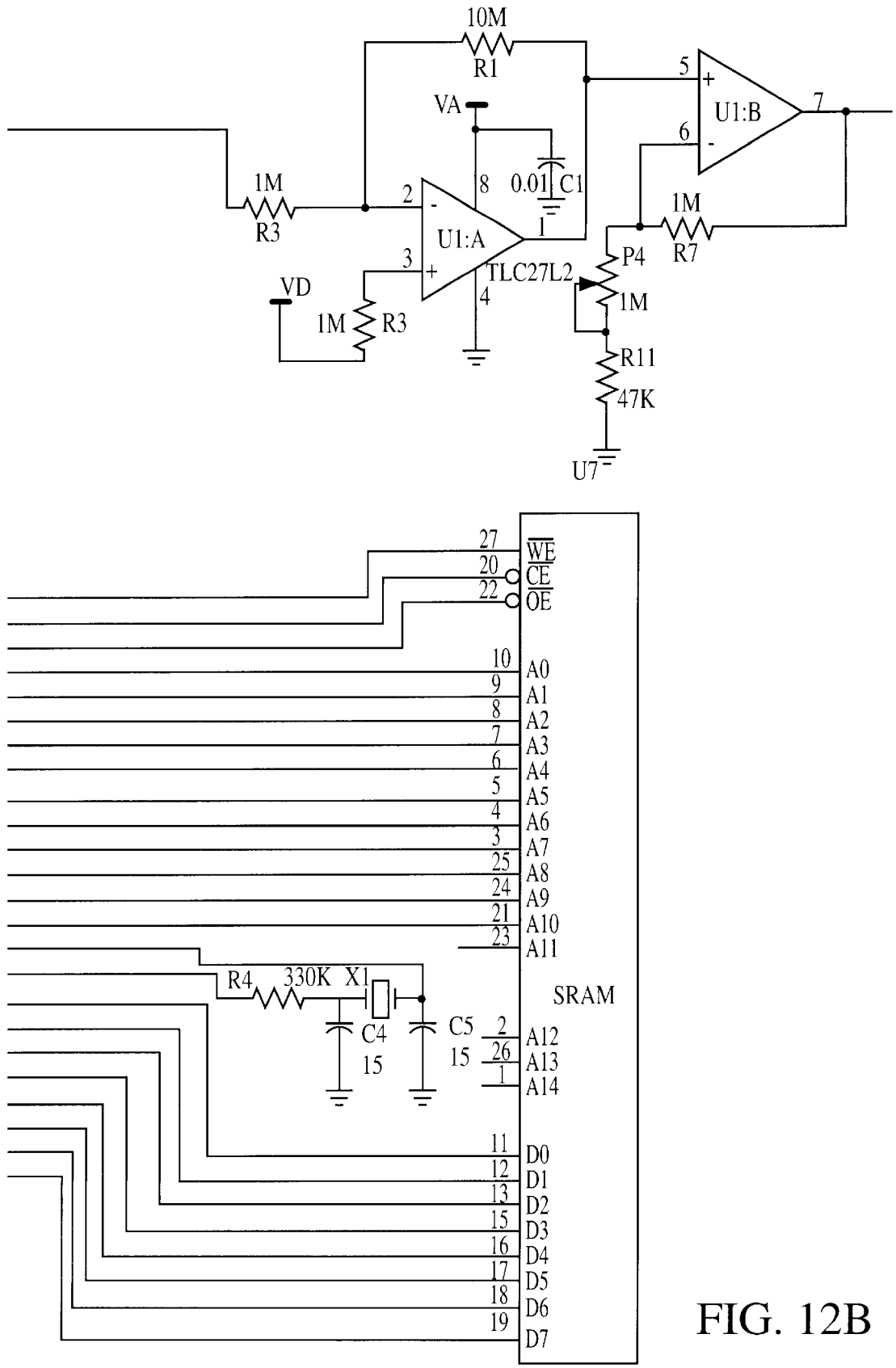
Figure 12C:
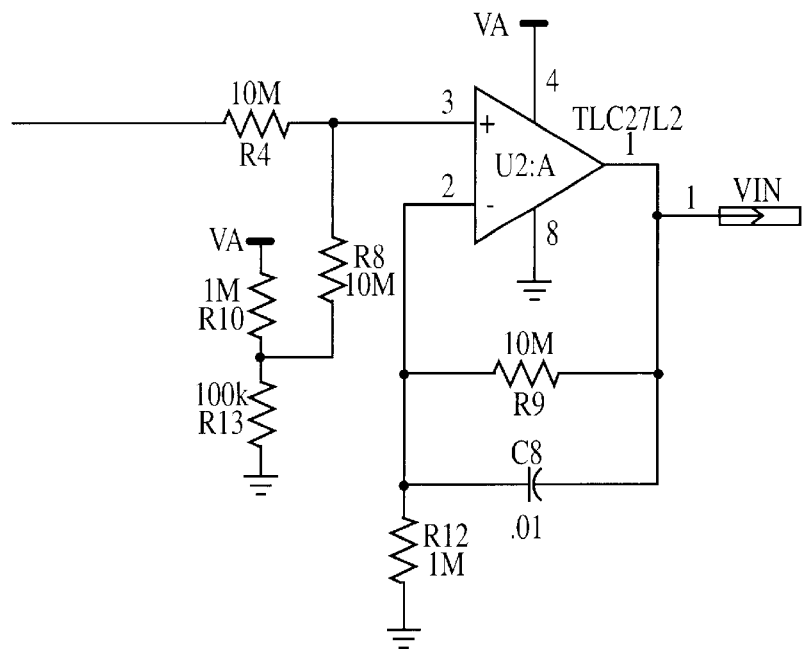

In a preferred embodiment of the present invention, the basic recorder 11 is illustrated in FIG. 12, which happens to show the schematic circuit diagram for the head worn recording unit. The circuit of this recorder is a basic representation of the other system recorders which are configured to accept appropriate sensors for various physiological measures and provide similar functional components, such as: (1) amplification and filtering of the sensor signal, (2) analog to digital conversion of the signal, (3) conditioning and storing of data values in memory, and (4) providing communications with a host computer for downloading data to the host computer or uploading control and patient information to the recorder.

When more than one sensor is contained in a site-specific recording unit (e.g., the thorax belt which provides sensors for respiration, chest activity and body position), all sensors are interfaced to a single microprocessor and the corresponding data can be stored in dedicated memory chips for each function or alternately stored in common memory. It should be noted that the inputs from the body position sensor can be directly connected to digital input ports of the microprocessor or configured to provide an analog voltage representation for input to the analog to digital converter.

The basic recorder 11 for each of the units includes: (a) an ultra-low power CMOS microprocessor controller 13 (Microchip PIC16C74) for timing and system control, (b) programmable memory, (c) signal conditioning and filtering circuitry, (d) an 8 bit, analog to digital (A/D) converter 14 for digitizing the analog signals, (e) 512K bytes or greater of SRAM, EEPROM or FLASH memory 15 for storing the digitized signals and (f) a mini jack 18 which allows connection to a smart cable 16 for communication to an external computer 17 system. Support components and circuit chips are of surface mount technology (SMT). The smart cable for use with this recorder consists of a miniplug at one end for connection to the recorder and a DB9 connector at the computer end. A very small SMT circuit board is contained within the DB9 shell and populated with an RS-232 UART chip to establish data communications between the recorder and the computer. Power is taken from the computer's serial port. Application software manages the data transfer and formats the data into a convenient file structure.

For monitoring the thorax and abdominal respiration motions of a subject utilizing the system shown in FIG. 5, the sensor of choice was selected to be a commercially-available, girth-measuring expansion belt assembly, such as a EPM Systems Model No. 1310 or a Pro-Tech Model No. 1461. These assemblies employ piezo-electric transducers, whereby simple stretching of the belt by respiratory motions produces an output signal proportional to the amount of stretching experienced by the belt.

If not properly adjusted and thereby allowed to be over or under stretched, these elastic belt assemblies can yield output signals whose amplitudes are attenuated and/or distorted. This can be a major problem since a reliable and accurate analysis of the subject's respiration is dependent on achieving good fidelity (both their relative amplitudes and their phase relationships) in the belt's output signals.

To attain this needed signal fidelity, high gain amplifier circuits with signal conditioning and filtering for piezoelectric transducers are added to the microprocessor based recorder that is used to record the belt's output signal.

For this sleep disorder monitoring work, the amplifier circuitry on the respiration units is adjusted to provide a band pass of about 0.15 to 0.50 hertz in order to measure the expected low frequency range of motions associated with respiratory movements, while filtering out the higher frequency range of one to ten hertz that is associated with general human activities. The A/D converters for the respiration recorders are set to sample their respective output signals at ten data points per second. Standard digital sampling techniques are employed to record the signals (<1 hertz).

Figure 1:
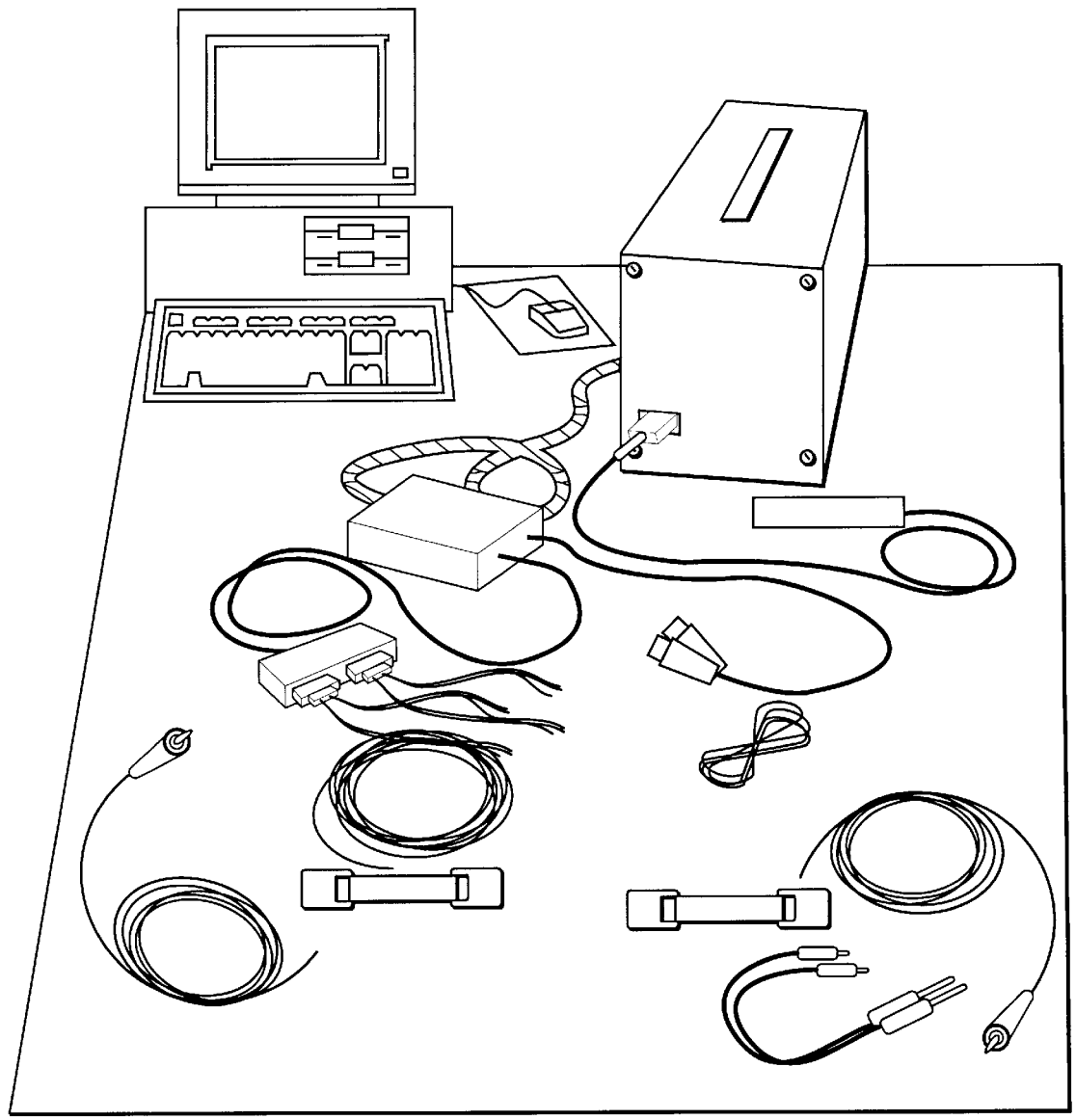
FIG. 1 shows the complexity of the sensors and electrode wires that are used with current, multi-channel, portable PSG systems.
Figure 2:
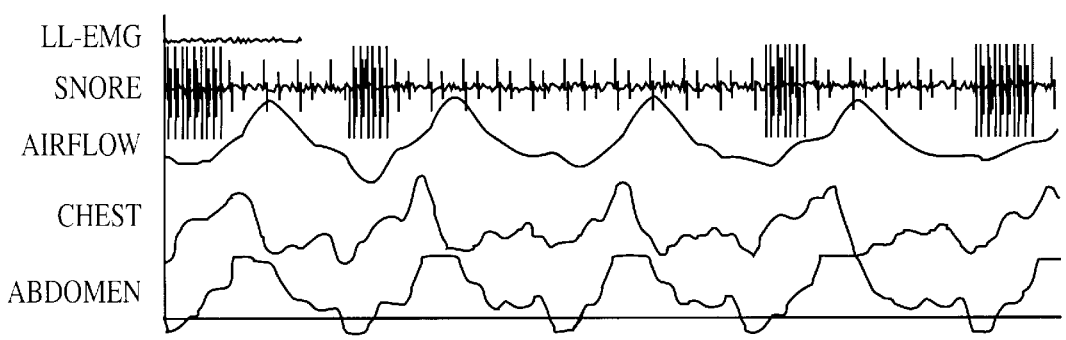
FIG. 2 shows the tracings provided by the manufacturer of the portable system shown in FIG. 1 for the temporal variations in airflow and respiration sensors located respectively at the patient's (1) mouth and nasal passageway, (2) chest, and (3) abdomen.

Additionally, the belt's signal fidelity was further enhanced by utilizing software on the host computer to apply an adaptive threshold correction to the belt's digitized signals. This feature minimizes belt-adjustment-related amplitude instabilities by automatically adjusting the detection threshold for signal changes lasting a minute or longer. Similarly, the signal gain control may be automatically calibrated so as to set the maximum amplitude swing of the breathing signal to prevent the type of signal clipping seen for the abdomen signal in FIG. 2.

For monitoring the upper airway breathing of a subject, a commercially-available, airflow sensor of the thermocouple type may be used, such a Pro-Tech cannula style, Model No. 1242, nasauoral airflow sensor or the Rochester Electro-Medical No. 602640 sensor assembly. Like the respiration sensors, the airflow sensor's output is recorded on a recorder having appropriate signal conditioning circuitry, and with additional front end circuit enhancements to ensure compatibility with the thermocouple's operating characteristics. The A/D converter for the airflow recorders is set to sample the output signals at ten data points per second. Standard digital sampling techniques are employed to record the signals (<1 hertz).

To distinguish between the periods when the subject is either awake or asleep, the general movements of a subject are monitored by utilizing a modified, commercially-available, IM System's PAM activity monitors/recorders. The technology for these recorders is revealed in U.S. Patent No. 5,749,372.

These recorders are modified by adding a mini-jack and reconfiguring the data download format to accommodate the smart cable transfer technology that is used with all the basic recorders. These recorders use a miniature, three-axis (triaxial) piezoelectric accelerometer sensor assembly to provide omni-directional movement detection. This three axis sensor features excellent linearity and resolution and uses two piezoelectric accelerometer bender units (Morgan Matroc No. 61416 PZT-5A) configured in a novel arrangement.

The two sensors are oriented to produce three dimensional (2 plane) measurements. They are so arranged to be orthogonal to one another respective to the longitudinal axis of acceleration. For the latitudinal axis of acceleration the sensors form a non parallel angle to a plane of the longitudinal axis and are oriented at an angle of twenty-five degrees from a vertical axis.

For this application, the recorders' signal conditioning circuitry is adjusted to provide a band pass of about one to ten hertz in order to measure the expected frequency range of activity associated with human activity. These recorders may be placed at multiple sites on the subject, including on the subject's wrist and chest.

Since an exact reproduction of the higher frequency (1–10 hertz), activity monitors' signals is not important, an alternate data sampling method may be used which requires less data storage space. The signal is sampled at a rate of forty per second and the sum (i.e., effective integration of the area under the curve) is stored in RAM every 0.1 seconds. This integration of the area under the curve is seen to give a measure that quantifies the magnitude and duration of the subject's activities.

To further aid in distinguish between the periods when the subject is either awake or asleep, an IM Systems three-dimensional (3D) body position monitor/recorder was used. This unit indicates when the patient is standing/sitting, reclining at 45 degrees or lying down, and when lying down, whether the patients is lying on his/her back, front, left or right side. This data proves to be especially useful in assessing sleep-wake states and identifying a patient's periods of sleepwalking. The technical details for this recorder/monitor are revealed in U.S. patent application Ser. No. 09/121,394, which was filed on Jul. 23, 1998.

A suitable mercury sensor for this monitor, which utilizes a recorder similar to the basic recorder previously described, has been found to be a modified version of the miniaturized Sandia Switch manufactured by Fifth Dimension, Inc., Trenton, N.J. This sensor consists of a globular shaped, glass envelope that measures approximately 1.3 cm in diameter and contains sixteen electrode posts, eight of which are used as active elements and eight of which are used as reference elements. These are equally spaced around the surface of the envelope to accurately register the physical position of the envelope relative to gravity.

Within this envelope, a pool of approximately 1000 mg of mercury covers the bottom-most group of electrode posts. As the sensor envelope is rotated, the mercury covered electrode groupings change and yield sensor outputs through the contacts. The information from the eight active elements gives 256 unique outcome values which are each matched with a truth table to determine the sensor's current position relative to gravity.

The output from this sensor with appropriate software detection and digital filter algorithms was found to be such as to allow one to distinguish and define forty basic body positions of interest. For the monitoring of patients with sleep disorders, it was found sufficient to utilize only six (i.e., patient lying supine, prone, or on right or left side, sitting, walking) of these forty positions to characterize the patient's body position and motion.

This sensor-positional-resolution capability was achieved by wiring each of the sensor's active electrode posts to the parallel input port of a computer. Eight-bit binary data values were then generated and stored as a reference truth table to establish a database of information identifying each rotational position of the sensor as the sensor was rotated in three dimensions. Additionally, for visual verification, the eight active electrode posts were connected through a battery to eight individual LED lights. The sensor was then rotated while noting which combinations of LEDs would light indicating which electrodes were contacting the pool of mercury residing at the bottom of the envelope. Each physical position relative to gravity presented a different pattern of lights. Shaking the envelope produced an effect in which all the LEDs would flash or sparkle, with the group of LEDs representing the dominate physical position glowing the brightest. Thus, no matter how much mercury splashing might be generated by walking or other motions, a software filter could easily distinguish the envelope's physical position.

For monitoring periodic limb movements such as those exhibited by patients with "restless legs syndrome," a modified, commercially available, IM Systems PAM-RL monitor/recorder is used. This recorder uses the three-axis piezo accelerometer sensor assembly and modifies the recorder by adding a mini-jack and reconfiguring the data download format to accommodate the smart cable transfer technology that is used with all the basic recorders. Additionally, the monitor has filtering capabilities that enable the unit to discriminate periodic from aperiodic leg movements This information permits discriminating these movements in relation to the occurrence of sleep apneas. This unit in combination with the PAM physical activity recorder at the wrist permits assessment of the number sleep disordered breathing events associated with arousal. It also permits extracting data associated with periodic leg movements from the wrist activity data that is used for detection of the sleep-wake states.

Because of the signal fidelity achieved with the present invention, it is possible to use a computer to accurately score the sleep events recorded using the present invention. In order to relate the results of such computer scoring with results that are achieved by use of the current, standard manual scoring methods, this computer scoring software was developed with the following special features: (1) a selectable time base for displaying signal wave forms in a paging format from 30 second (i.e., the typical PSG polygraph display) to 60 minute screens, (2) a page reference numbering system which can be set to match polygraph page numbers, (3) forward and backward paging, (4) an option to skip a specified time either by selection with cursor or by specifying the desired minutes to step forward/backward, (5) selectable signal threshold level and time duration for detection of apnea events, (6) markers to flag start and stop times of candidate events recorded on the various recorder channels, (7) detection schemes based on single or multiple variables, (8) listing of apnea events and possible events by type, time, duration, page number based on respiration or activity, (9) total number of events for each hour of sleep, (10) histograms and summary plots, (11) capability to export data to spreadsheets, (12) capability to print out the data, and (13) complete user friendly control of all parameter, threshold and analysis functions.

For computer scoring, sleep disorder breathing events (DBEs) are characterized as being either central, obstructive or mixed and as apneas or hypopneas, wherein these distinctions are based upon airflow and respiration effort measurements requiring: decreases for both measures to detect a hypopnea, cessation of effort and airflow for a central apnea, cessation of airflow with continued effort for an obstructive apnea and a paradoxical respiration effort change with decreased airflow for an obstructive hypopnea. See FIGS. 6–8 for examples of computer generated displays of the respiration and airflow analog signals corresponding to such DBEs.

The computer assisted scoring programs calculate basic sleep related information, including: DBE per hour, type of DBE and its duration and whether chest body-movement activity occurred during the event. Statistics are determined for each body position used by the patient.

Figure 6:
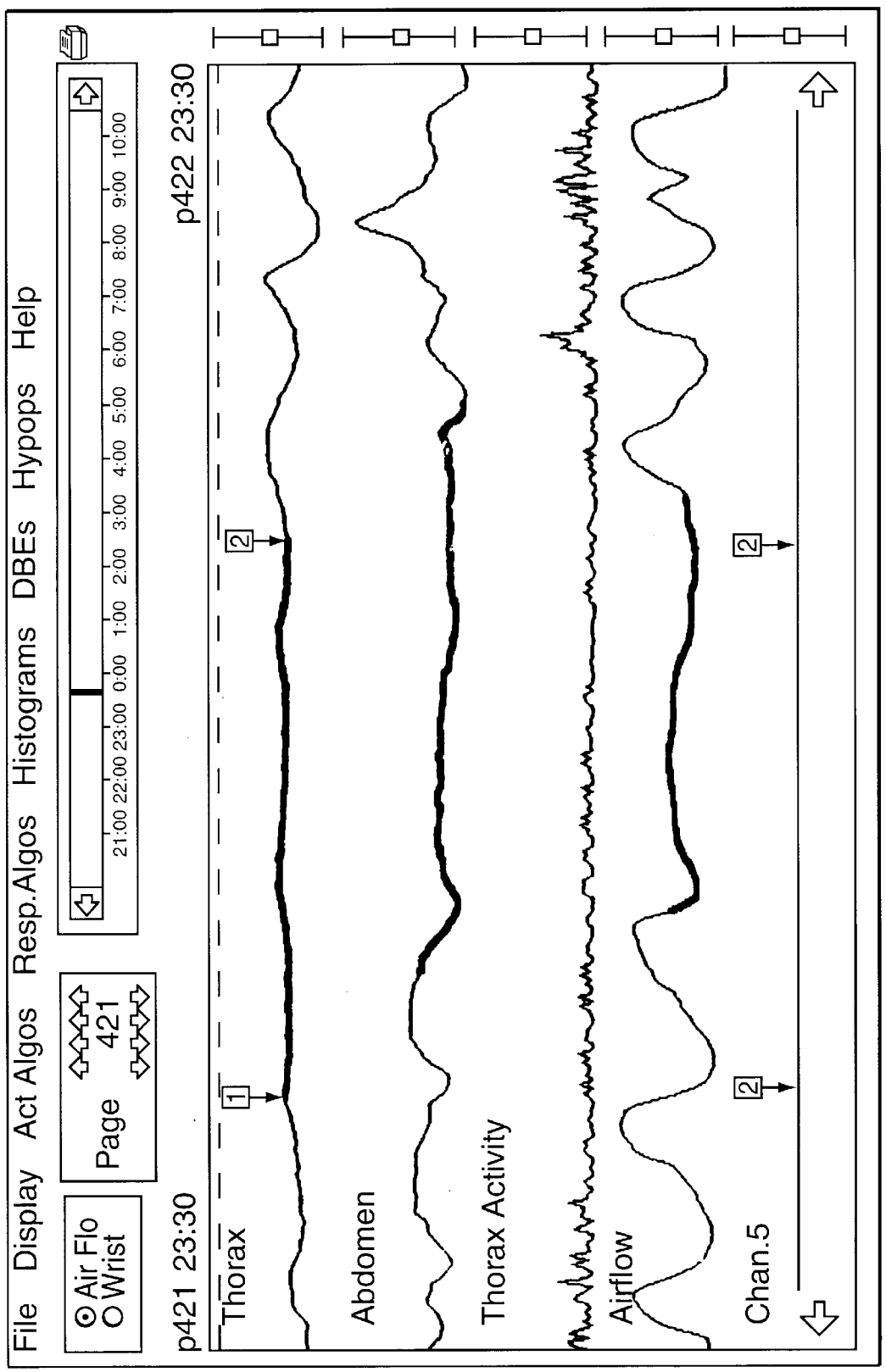
FIG. 6 shows a computer screen display generated with the software of the present invention that illustrates the occurrence of a central DBE.

The detection algorithm for a central DBE, shown in FIG. 6, consists of finding the maximum and minimum signal levels in a menu-specified "time step," typically five seconds. The time step is used to capture the high and low points of a single breath on a channel with varying DC offsets. A potential DBE begins when a "max-min" point falls below a menu-specified threshold and ends when it rises above the same threshold. This threshold is set in terms of a percentage of a "baseline amplitude" (DC level). This is the average max-min" value determined at the start of the record.

In recordings where changes in expansion belt baseline sensitivity are observed (i.e., an unnatural sustained decrease of respiration amplitude caused by belt displacement), an "adaptive threshold" algorithm is used. It involves slowly adjusting the baseline amplitude throughout the record while maintaining a fixed percentage of this baseline as the threshold. The scheme used to adjust the baseline in this preferred embodiment was a 3 db/octave low-pass filter working on the time-step max-mins with a time constant of typically several minutes.

To further improve upon the accuracy of the determination of the start and end time for such central DBE, a "scanback" algorithm may be applied after the event is detected. This involves measuring and saving the max-min points over shorter intervals and scanning back into these saved points to correct the onset time. A similar scheme is used to correct the end time.

Figure 7:
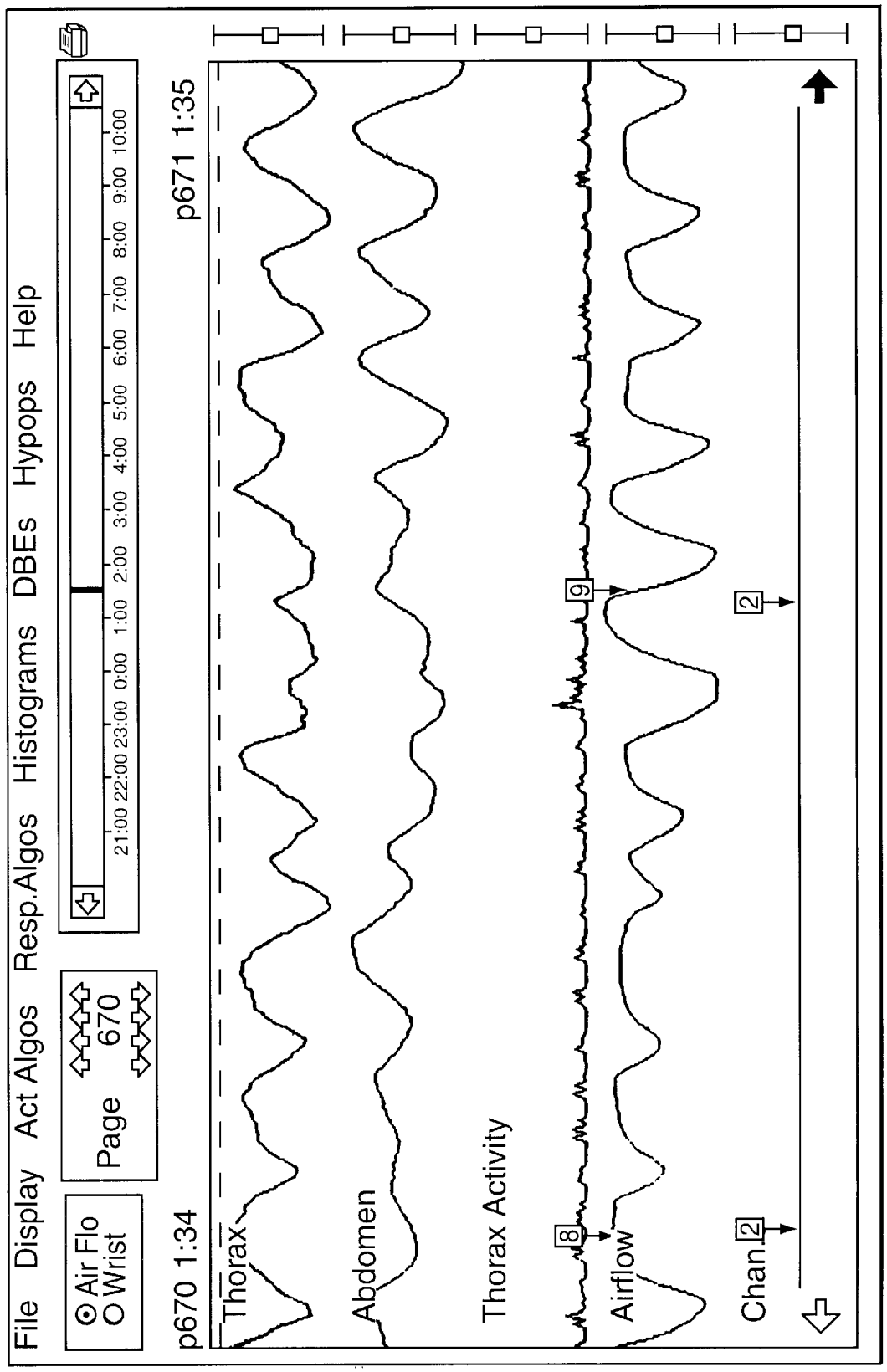
FIG. 7 shows a computer screen display generated with the software of the present invention that illustrates the occurrence of a hypopnea DBE.

A hypopnea DBE, as shown in FIG. 7, is defined to occur when airflow and respiration efforts decrease by a certain percentage of their normal values, typically about 50%, and last for ten seconds or more. The detection algorithm for a hypopnea DBE is basically the same as for the central DBE in that it determines when max-min points from the respiration and airflow channels fall below predefined thresholds. A similar scanback routine is also used. The major difference for the hypopnea DBE lies in detecting a much smaller decrease in signal amplitude, requiring a more sophisticated adaptive-threshold scheme. With this algorithm, a "stack" (first in-first out list) holds all the max-min points for an "adaptive period," typically a few minutes. For every time-step, a new max-min point is pushed onto the stack displaying the oldest. Then, periodically (typically every 10–15 seconds) the stack is sorted and the max-min value at a certain percentile (typically, the 80th) is taken to be the new adaptive baseline. From this, new percentage thresholds are derived.

Figure 8:
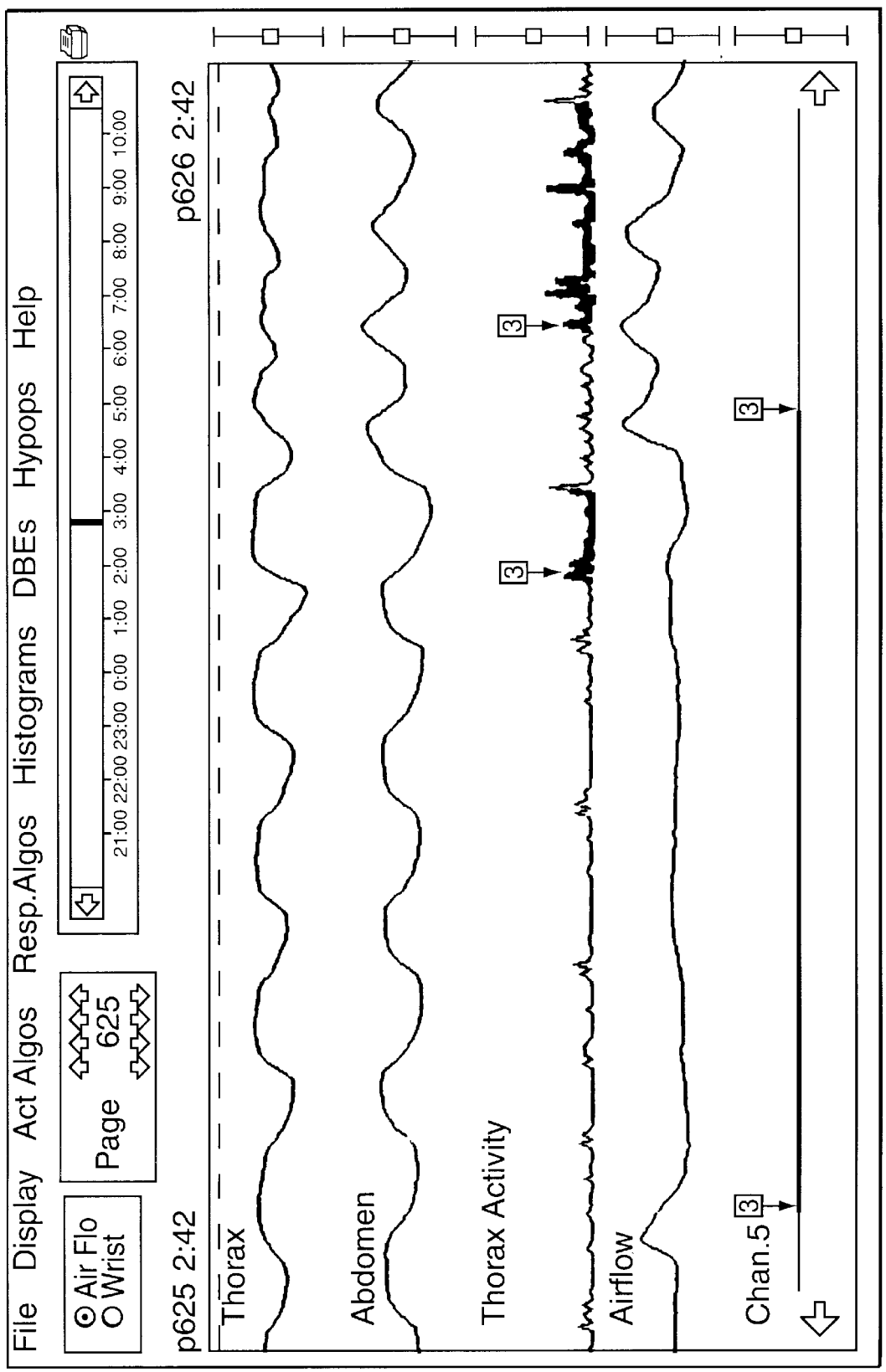
FIG. 8 shows a computer screen display generated with the software of the present invention that illustrates the occurrence of an obstructive DBE.

An obstructive DBE, as shown in FIG. 8, is defined to occur when the breathing motions of the thorax and abdomen are out of phase and there is a cessation of airflow. A menu-selected threshold is used to set this defining phase shift percentage. The algorithm for detecting obstructive DBE determines the positive slope of the thorax respiration signal (inhalation) and compares this with the negative slope of the abdomen respiration signal. If the phase is augmented more than the threshold setting and the event lasts for longer than ten seconds, it is defined as an obstructive DBE. If the out of phase condition continues for less than ten seconds but is coupled with a second out of phase event occurring with a menu-selected time period that exceeds ten seconds, then the two events are merged and considered one event. Additionally, if the thorax and abdomen are out of phase for less than ten seconds, but during this same period the airflow sensor indicates a reduced airflow extending ten or more seconds, then this event is deemed to be an obstructive DBE.

Figure 9:
FIG. 9 shows a computer screen display generated with the software of the present invention that illustrates a listing of all DBE identified during the monitoring period, with information on DBE events by type, time duration, page number on which the data record exists and whether high frequency chest-body movement activity occurred during these events.

In a preferred embodiment, the present invention's software provide a comprehensive array of menu, detection, data and screen displays. Included is a DBE list that posts all possible apnea/DBE events by type, time duration, page number in which the data record exists and whether high frequency chest-body movement activity occurred during these events. See FIG. 9. The software provides that simply clicking on any data point will take you to the appropriate page for viewing analysis.

Figure 10:
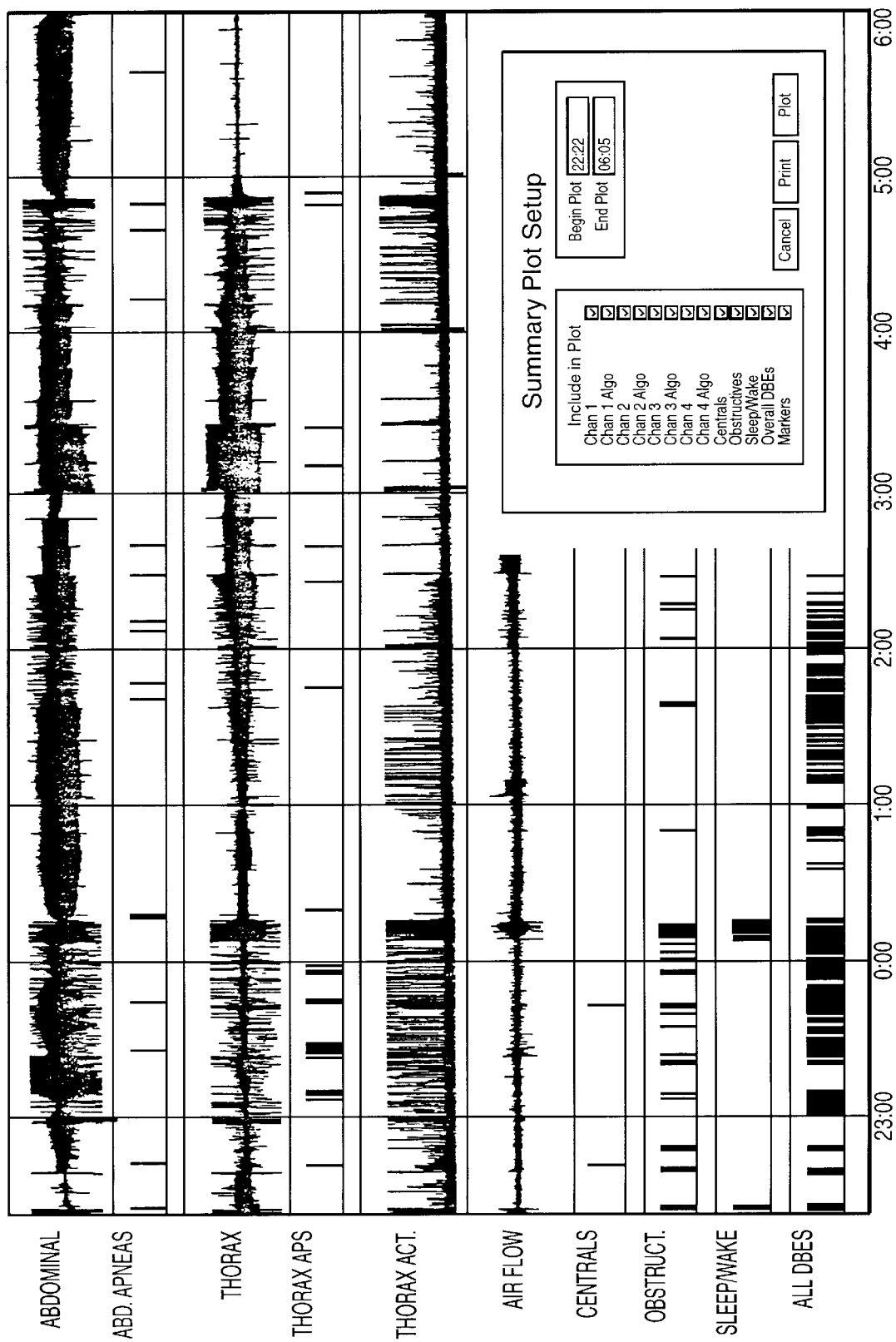
FIG. 10 shows a computer screen display generated with the software of the present invention that illustrates a plot that summarizes all the recorded data for up to a specified duration.

Additionally, the invention's software provides a summary plot that summarizes all data for up to a specified duration, typically ten hours. This includes data for the thorax and abdomen respiration rates, airflow rate, and thorax activity levels, the identification of the time when central, obstructive or hypopnea DBE occurred, and the identification of periods when the patient was asleep or awake as determined by the wrist activity monitor. See FIG. 10.

The task of distinguishing between the states of the patient being awake or asleep is accomplished by utilizing the signal from the IM Systems' PAM wrist activity recorder, with the change from wake to sleep state being defined by when activity over a three minute period falls below a threshold, sleep criteria level. Similarly, the change to waking is defined to occur when the activity over a three minute period is greater than a set wake criteria level, where this level increases with duration of maintained sleep and sleep criteria level decreases with increasing duration of maintained wakefulness.

This determination of the sleep or awake state is more complicated for sleep apnea patients in that they often exhibit periodic arousals and movements after each apnea event without actually being awake. Thus, it becomes important for such patients to exclude their respiration related events from sleep-wake determinations. This was accomplished by denoting DBEs with the use of the airflow and respiration signals and then excluding a fixed period of time after such events from the sleep-wake determinations.

Periods of general activity are determined by utilizing the signals from the wrist and thorax recorders and applying a "Holds On" algorithm to these signals. This algorithm looks for physical activity above a menu-specified threshold and followed by pre-set periods of no activity. The onset of activity is flagged when the signal exceeds threshold and again when it falls below threshold. This determines the duration of the hold-on period.

Figure 11:
FIG. 11 shows a computer screen used for setting the various algorithm parameters involved in identifying the activity periods associated with specific apnea events.

Activity periods are then filtered by a "Duration Length" algorithm which looks for periods of less than sixty seconds, preceded and succeeded by menu-selected number of seconds with no activity. This algorithm is designed to give separate activity periods for individual apnea events. FIG. 11 displays a computer screen that may be used for setting the various parameters used in these algorithms.

The software of the present invention allows the wake state as determined from the wrist recorder to be marked in epoch form by the computer, with further adjustments possible by a PSG technician. Sleep-wake data from the wrist recorder includes: total sleep time, sleep efficiency (from sleep onset), wake after sleep onset and wake periods greater than a minimum criteria which was set to exclude the sleep disordered breathing events.

It will be appreciated that the ambulatory, distributed recorders system 10 disclosed herein is seen to achieve its primary object of providing an improved means for diagnosing the medical conditions of fully ambulatory patients.

For patients experiencing excessive sleepiness, a preferred embodiment of the present invention has been disclosed that: (1) provides a broad spectrum of PSG data not heretofore available for the fully ambulatory patient, (2) eliminates the requirement that patients must be outfitted with an array of tethered electrode wires and sensors for connection to bulky body monitors or table-top consoles situated in clinical laboratories, (3) is designed for unattended use—a technician need not come to the home for set-up, disconnection and data retrieval, and (4) eliminates the need for the subjective analysis of the data by highly trained, sleep professionals.

Although the foregoing disclosure relates to preferred embodiments of the invention, it is understood that these details have been given for the purposes of clarification only. Various changes and modifications of the invention will be apparent, to one having ordinary skill in the art, without departing from the spirit and scope of the invention as hereinafter set forth in the claims.

We claim:

1. A method for aiding in the diagnosis of the medical condition of a fully ambulatory subject who exhibits temporal variations in various physiological parameters as a result of experiencing sleep disordered breathing events, comprising the steps of:

locating a separate, recording unit on a plurality of selected measurement sites of the subject, wherein said recording units each having a physiological parameter sensor with signal conditioning and filtering circuitry to yield required levels of signal fidelity, a programmable controller with an analog to digital converter and an integrated data storage recorder, using said units to collect sensor output data that quantifies the temporal variations in the physiological parameter of interest at each said measurement site, sampling sensor output data at prescribed time intervals, time stamping and storing said sampled data in said integrated recorders, providing said units with a smart input/output interface device to control data flow between said recorders and an external computer, while allowing for the time synchronization of the collection of data from said units, using said external computer with application software to analyze and display the temporal variations in said data for the purpose of assessing the medical condition of said subject, using said external computer to score sleep disorder breathing events recorded within said data, and wherein said sleep disorder breathing events are characterized as being either central, obstructive or mixed events and as apneas or hypopneas, wherein said characterizations are based upon airflow and abdomen and thorax respiration effort measurements, with a hypopnea being defined by decreases amounting to less than a total cessation in all said measures, with a central apnea being defined by a cessation of all said measures, with an obstructive apnea being defined as a cessation of airflow with continued respiration efforts, and with an obstructive hypopnea being defined as paradoxical respiration effort changes with a decrease in airflow less than a total cessation.

2. A method for aiding in the diagnosis of the medical condition of a fully ambulatory subject, as recited in claim 1, wherein:

a detection algorithm for said central sleep disordered breathing event entails finding the difference between the maximum and minimum values of said recorded measures in the successive time steps that comprise the period over which said data was recorded and comparing said differences with a specified threshold value, with a central disordered breathing event being defined as beginning when said differences falls below said threshold value and ends when said difference rises above the same threshold value.

3. A method for aiding in the diagnosis of the medical condition of a fully ambulatory subject, as recited in claim 2, further comprising the step of using an adaptive threshold algorithm in said data analysis to compensate for changes in the baseline amplitude of the temporally varying signals, wherein said adaptive threshold algorithm is defined by slowly adjusting the baseline amplitude throughout the record by employing a low-pass filter having a time constant of greater than five minutes to said signals representing the differences determined for said successive time steps while maintaining a fixed percentage of this baseline as the threshold.

4. An ambulatory distributed recorders system for aiding in the diagnosis of the medical condition of a fully ambulatory subject who exhibits temporal variations in various physiological parameters as a result of said medical condition said system comprising:

a plurality of separate, self-contained, recording units, said units located on a plurality of selected measurement sites of the subject, wherein said recording units each having a physiological parameter sensor with signal conditioning and filtering circuitry to yield required levels of sensor signal fidelity, said sensor and circuitry being connected to a programmable controller, said controller connected to and controlling an analog to digital converter and a data storage recorder, wherein said controller controls the sampling of said sensor signal at prescribed time intervals, and time stamps and stores said sampled data in said recorder, an external computer, a mini jack connected to said programmable controller that allows communication to said external computer, and a smart input/output interface device connectable to said mini jack for controlling data flow between said recorders and said external computer, while allowing for the time synchronization of the collection of data from said units.

5. An ambulatory distributed recorders system as recited in claim 4, further comprising:

application software that runs on said external computer to control the analysis of the temporal variations in said data for the purpose of diagnosing the medical condition of said subject.

6. An ambulatory distributed recorders system as recited in claim 5, wherein:

said units for use in diagnosing subjects with sleep disorders are chosen from among the group of units consisting of: thorax respiration effort unit located on chest, body position unit located on chest, level of physical activity unit located on chest, airflow unit located on head, eye blink unit located on head, abdomen respiration effort unit located on abdomen, level of physical activity unit located on wrist, periodic leg movement unit located on ankle, pulse-oximeter unit located on wrist, electroencephalogram unit located on head, electromyographic unit located at various location on the subject's body, and a body motion frequency unit located on the subject's limbs or other body sites.

7. An ambulatory distributed recorders system as recited in claim 6, wherein:

said external computer is used to score sleep disorder breathing events recorded within said data.

8. An ambulatory distributed recorders system as recited in claim 5, wherein:

said units for use in diagnosing subjects with sleep disorders are chosen from among the group of units consisting of: thorax respiration effort unit located on chest, body position unit located on chest, level of physical activity unit located on chest, airflow unit located on head, eye blink unit located or head, abdomen respiration effort unit located on abdomen, level of physical activity unit located on wrist, and periodic leg movement unit located on ankle, pulse-oximeter unit located on wrist, electroencephalogram unit located on head, electromyographic unit located at various location on the subject's body, and a body motion frequency unit located on the subject's limbs or other body sites.

9. An ambulatory distributed recorders system as recited in claim 8, wherein:

said sleep disorder breathing events are characterized as being either central, obstructive or mixed events and as apneas or hypopneas, wherein said characterizations are based upon said airflow and abdomen and thorax respiration effort measurements, with a hypopnea being defined by decreases amounting to less than a total cessation in all said measures, with a central apnea being defined by a cessation of all said measures, with an obstructive apnea being defined as a cessation of airflow with continued respiration efforts, and with an obstructive hypopnea being defined as paradoxical respiration effort changes with a decrease in airflow less than a total cessation, and said computer scoring of sleep disorder breathing events utilizes a detection algorithm for said central sleep disordered breathing event, wherein said detection algorithm entails finding the difference between the maximum and minimum values of said recorded measures in the successive time steps that comprise the period over which said data was recorded and comparing said differences with a specified threshold value, with a central disordered breathing event being defined as beginning when said differences falls below said threshold value and ends when said difference rises above the same threshold value.

10. An ambulatory distributed recorders system as recited in claim 9, wherein:

said computer scoring of sleep disorder breathing events further comprising the use of an adaptive threshold algorithm in said data analysis to compensate for changes in the baseline amplitude of the temporally varying signals, wherein said adaptive threshold algorithm is defined by slowly adjusting the baseline amplitude throughout the record by employing a low-pass filter having a time constant of greater than five minutes to said signals representing the differences determined for said successive time steps while maintaining a fixed percentage of this baseline as the threshold.

11. An ambulatory distributed recorders system as recited in claim 4, wherein: said units for use in diagnosing subjects with sleep disorders are chosen from among the group of units consisting of: thorax respiration effort unit located on chest, body position unit located on chest, level of physical activity unit located on chest, airflow unit located on head, eye blink unit located on head, abdomen respiration effort unit located on abdomen, level of physical activity unit located on wrist, periodic leg movement unit located on ankle, pulse-oximeter unit located on wrist, electroencephalogram unit located on head, and an electromyographic unit located at a location on the subject's body.

* * * * *